United States Patent
Bok et al.

(10) Patent No.: US 6,313,171 B1
(45) Date of Patent: Nov. 6, 2001

(54) METHOD FOR PREVENTING OR TREATING ELEVATED BLOOD LIPID LEVEL-RELATED DISEASES BY ADMINISTERING CINNAMIC ACID DERIVATIVES

(75) Inventors: Song-Hae Bok; Tae-Sook Jeong; Ki-Hwan Bae, all of Daejeon; Yong-Bok Park; Myung-Sook Choi, both of Daegu; Surk-Sik Moon, Gongju-shi; Yong-Kook Kwon, Daejeon; Eun-Sook Lee, Daejeon; Byung-Hwa Hyun, Daejeon; Yang-Kyu Choi, Daejeon; Chul-Ho Lee, Daejeon; Sae-Bom Lee, Daejeon; Young-Bae Park, Seoul; Hyo-Soo Kim, Seoul, all of (KR)

(73) Assignee: Korea Research Institute of Bioscience & Biotechnology, Daejeon (KR)

( * ) Notice: Subject to any disclaimer, the term of this patent is extended or adjusted under 35 U.S.C. 154(b) by 0 days.

(21) Appl. No.: 09/396,312

(22) Filed: Sep. 15, 1999

(30) Foreign Application Priority Data

Sep. 15, 1998 (KR) .................................. 98-37960

(51) Int. Cl.⁷ ......................... A61K 31/19; A61K 31/235

(52) U.S. Cl. .......................................... 514/568; 514/532

(58) Field of Search ...................... 514/537, 568

(56) References Cited

U.S. PATENT DOCUMENTS 3,739,015   6/1973   Wattanabe et al. .............. 260/473 R

FOREIGN PATENT DOCUMENTS 2117376   10/1971   (DK) .

OTHER PUBLICATIONS

Watanabe et al. Studies of Hypolipidemic Agents. Synthesis and Hypolipidemic Activities of Alkoxycinnamic Acid Derivatives, J. Med. Chem. 1980, vol. 23, pp. 50–59, ISSN 0022–2623, Abstract; p. 51, col. 2, paragraph 3.

Primary Examiner—Theodore J. Criares
Assistant Examiner—Jennifer Kim
(74) Attorney, Agent, or Firm—Rosenman & Colin LLP

(57) ABSTRACT

A method for treating or preventing an elevated blood lipid level-related disease such as hyperlipidemia, arteriosclerosis, angina pectoris, stroke and hepatic diseases in a mammal, which comprises administering thereto an effective amount of a cinnamic acid derivative of formula Ia or Ib, or a pharmaceutically acceptable salt thereof:

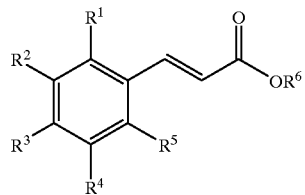

(Ia)

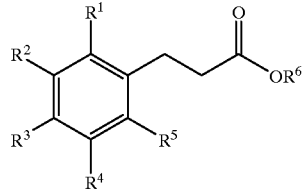

(Ib)

wherein, $R^1$, $R^2$, $R^3$, $R^4$ and $R^5$ are independently H, OH or $C_{1-4}$ alkoxy; and $R^6$ is H, $C_{1-4}$ alkyl group, or $C_{5-7}$ cycloalkyl group having one or more substituents selected from the group consisting of OH, alkoxy and carboxy groups.

13 Claims, 10 Drawing Sheets

METHOD FOR PREVENTING OR TREATING ELEVATED BLOOD LIPID LEVEL-RELATED DISEASES BY ADMINISTERING CINNAMIC ACID DERIVATIVES

FIELD OF THE INVENTION

The present invention relates to a method for treating or preventing elevated blood lipid level-related diseases such as hyperlipidemia, arteriosclerosis, angina pectoris, stroke and hepatic diseases in a mammal, which comprises administering an effective amount of a cinnamic acid derivative thereto.

BACKGROUND OF THE INVENTION

It has been reported that blood lipids, especially cholesterol and triglycerides, are closely related to various kind of diseases such as coronary cardio-circulatory diseases, e.g., arteriosclerosis and hypercholesterolemia, and fatty liver. Cholesterol, a fatty steroid alcohol, is a blood lipid produced from saturated fat in the liver. Triglycerides are another type of blood lipids which are known to increase the risk of various diseases. It has also been reported that an elevated blood or plasma cholesterol level causes the deposition of fat, macrophages and foam cells on the wall of blood vessels, such deposit leading to plaque formation and then to arteriosclerosis (see Ross, R., *Nature*, 362, 801–809(1993)). One of the methods for decreasing the plasma cholesterol level is alimentotherapy to reduce the ingestion of cholesterol and lipids. Another method is to inhibit the absorption of cholesterol by inhibiting enzymes involved therein.

Acyl CoA-cholesterol-o-acyltransferase (ACAT) promotes the esterification of cholesterol in blood. Foam cells are formed by the action of ACAT and contain a large amount of cholesterol ester carried by low density lipoproteins. The formation of foam cells on the wall of artery increases with the ACAT activity, and, accordingly, an inhibitor of ACAT may also be an agent for preventing arteriosclerosis. Further, it has been reported that the blood level of LDL-cholesterol can be reduced by inhibiting the ACAT activity (see Witiak, D. T. and D. R. Feller (eds.), *Anti-Lipidemic Drugs: Medicinal, Chemical and Biochemical Aspects*, Elsevier, pp159–195 (1991)).

Further, it has been reported that hypercholesterolemia can be treated effectively by reducing the rate of cholesterol biosynthesis through the inhibition of cholesterol ester transfer protein (CETP) which mediates the cholesterol transfers between the lipoproteins, or 3-hydroxy-3-methylglutaryl coenzyme A (HMG-CoA) reductase which mediates the synthesis of mevalonic acid, an intermediate in the biosynthesis of sterols or isoprenoids (see *Cardiovascular Pharmacology*, William W. Parmley and Kanu Chatterjee Ed., Wolfe Publishing, pages 8.6–8.7, 1994).

Therefore, numerous efforts have been made to develop medicines to inhibit HMG-CoA reductase; and, as a result, several compounds derived from Penicillium sp. and Aspergillus sp. have been commercialized. Specifically, Lovastatin® and Simvastatin® developed by Merck Co., U.S.A., and Pravastatin® developed by Sankyo Co., Japan, have been commercialized (see C. D. R. Dunn, *Stroke: Trends, Treatment and Markets*, SCRIPT Report, PJB Publications Ltd., 1995).

However, these medicines are very expensive and a long-term administration thereof is known to induce an adverse side effect to the central nervous system. Further, although Lovastatin® and Simvastatin® may reduce the plasma LDL cholesterol level by enhancing the activity of LDL receptor in the liver, they cause side effects such as increase in creatine kinase in the liver and rhabdomyolysis (see Farmer, J. A., et al., Baillers-clin. Endocrinol. Metal., 9, 825–847(1995)). Accordingly, there has continued to exist a need to develop an inexpensive and non-toxic inhibitor of HMG-CoA reductase.

Another example of the elevated blood-lipid level-related disease is fatty liver. In particular, the excessive intake of fat-containing foods and alcohol causes fatty liver wherein a large amount of lipids is deposited in the liver tissue and the levels of serum GOT (glutamate-oxaloacetate transaminase), GPT (glutamate-pyruvate transaminase) and γ-GTP (γ-glutamyl transpeptidase) are elevated (see T. Banciu et al., *Med. Interne.*, 20, 69–71(1982); and A. Par et al., *Acta. Med. Acad. Sci. Hung.*, 33, 309–319(1976)). Hayashi et al. has reported that an extract from green tea improved liver function in a rat by preventing the elevation of serum GOT and GPT (M. Hayashi et al., *Nippon Yakuri gaku Zasshi*, 100, 391–399(1992)).

Fat accumulates in the liver mainly in the form of triglycerides and fatty acids, and also to a minor extent, in the form of cholesterol. Further, it has been reported that one of the major signs of fatty liver is high blood cholesterol and/or triglyceride contents. Therefore, fatty liver is closely related to the level of cholesterol and/or triglycerides in the blood.

Bioflavonoids are polyphenolic antioxidants which exist widely in the natural world, especially in vegetables, fruits, wine and the like. It has been reported that the bioflavonoids exhibit various useful pharmacological activities such as anti-inflammatory, capillary reinforcing, anti-oxidative, anti-cancer, anti-viral and anti-platelet aggregation activities (see O. Benavente-Garcia et al., Uses and properties of citrus flavonoids, *J. Aqr. Food Chem.*, 45, 4506–4515, 1997).

The present inventors have endeavored to develop a novel pharmacological use of bioflavonoids which are abundantly present in herbs, foodstuffs, vegetables and fruits. As a result, it has been discovered that cinnamic acid and hydrocinnamic acid derivatives, which are employed as precursors in the biosynthesis of bioflavonoids and forms a backbone structure of bioflavonoids, are effective in treating or preventing elevated blood lipid level-related diseases. Specifically, it can greatly reduce plasma cholesterol level; prevent the activities of HMG-CoA reductase and ACAT; inhibit the accumulation of macrophage-lipid complex on the endothelial wall of an artery; and prevent hepatic dysfunctions in a mammal.

SUMMARY OF THE INVENTION

Accordingly, it is a primary object of the present invention to provide a method for treating or preventing an elevated blood lipid level-related disease.

In accordance with one aspect of the present invention, there is provided a method for treating or preventing an elevated blood lipid level-related disease, which comprises administering thereto an effective amount of a cinnamic acid derivative of formula Ia or Ib, or a pharmaceutically acceptable salt thereof:

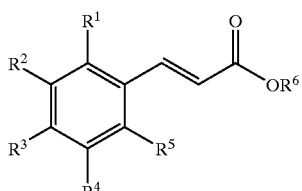

(Ia)

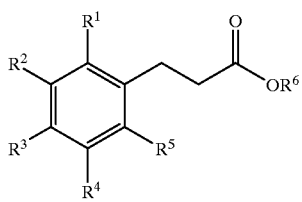

(Ib)

wherein,

R$^1$, R$^2$, R$^3$, R$^4$ and R$^5$ are independently H, OH or C$_{1-4}$ alkoxy; and R$^6$ is H, C$_{1-4}$ alkyl, or C$_{5-7}$ cycloalkyl having one or more substituents selected from the group consisting of OH, alkoxy and carboxy groups.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1A:
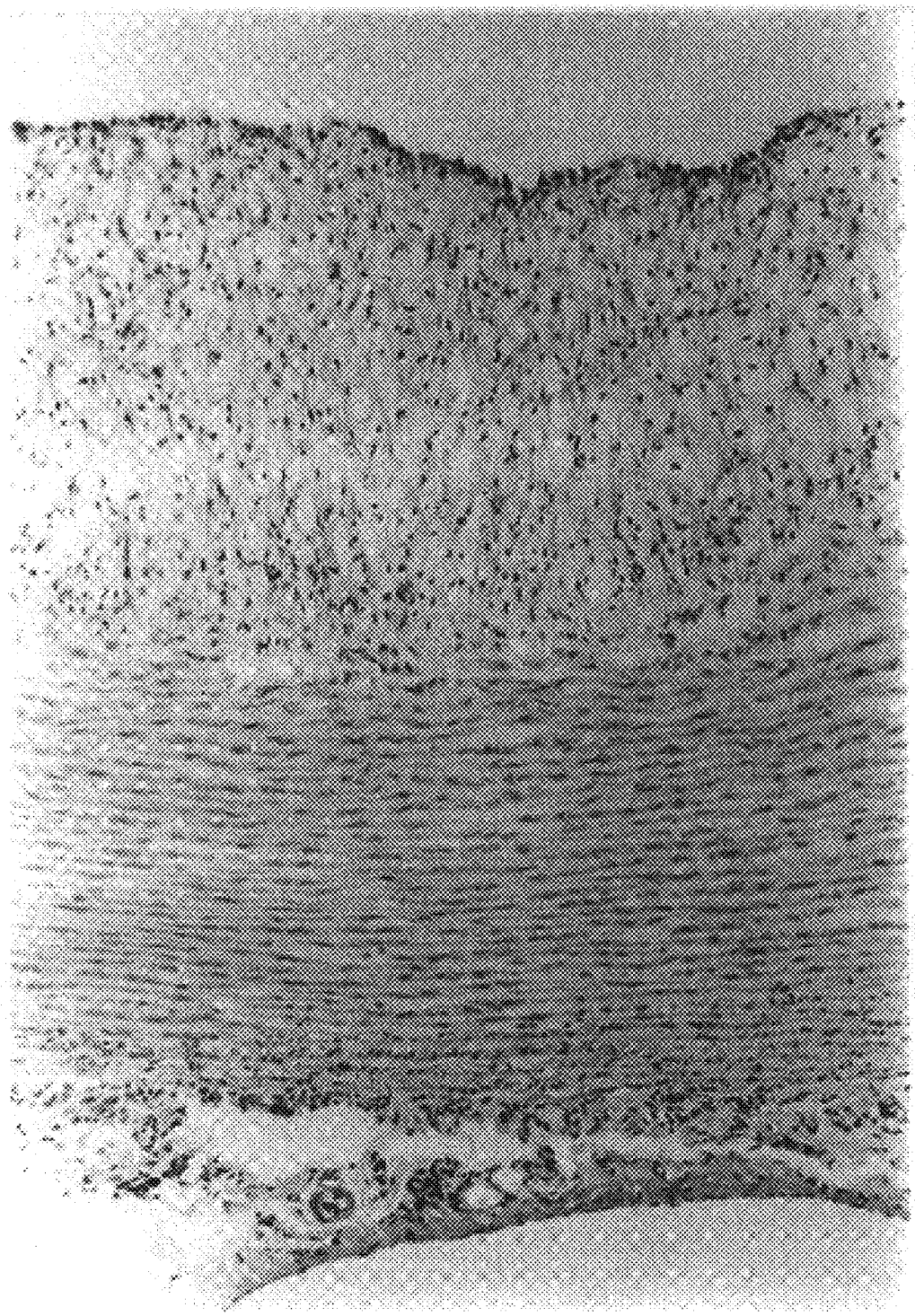
FIGS. 1A, 1B, 1C, 1D and 1E show the arterial endothelium of the rabbits administered with 1% cholesterol; 1% cholesterol plus 1 mg/kg Lovastatin®; 1% cholesterol plus 0.1% 4-hydroxycinnamic acid; 1% cholesterol plus 0.1% 3,4-dihydroxycinnamic acid; and 1% cholesterol plus 0.1% 3,4-dihydroxyhydrocinnamic acid, respectively.
Figure 1B:
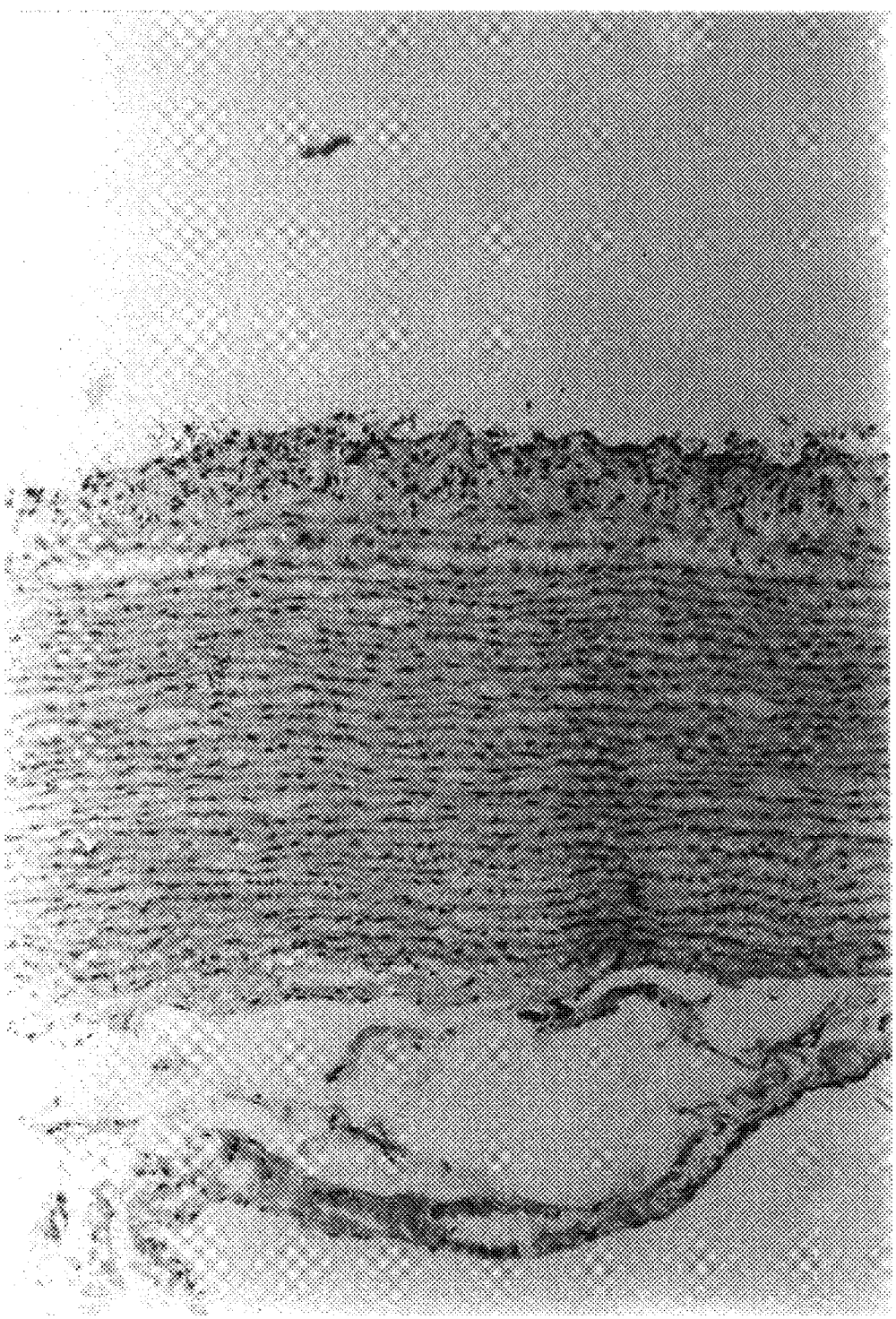
Figure 1C:
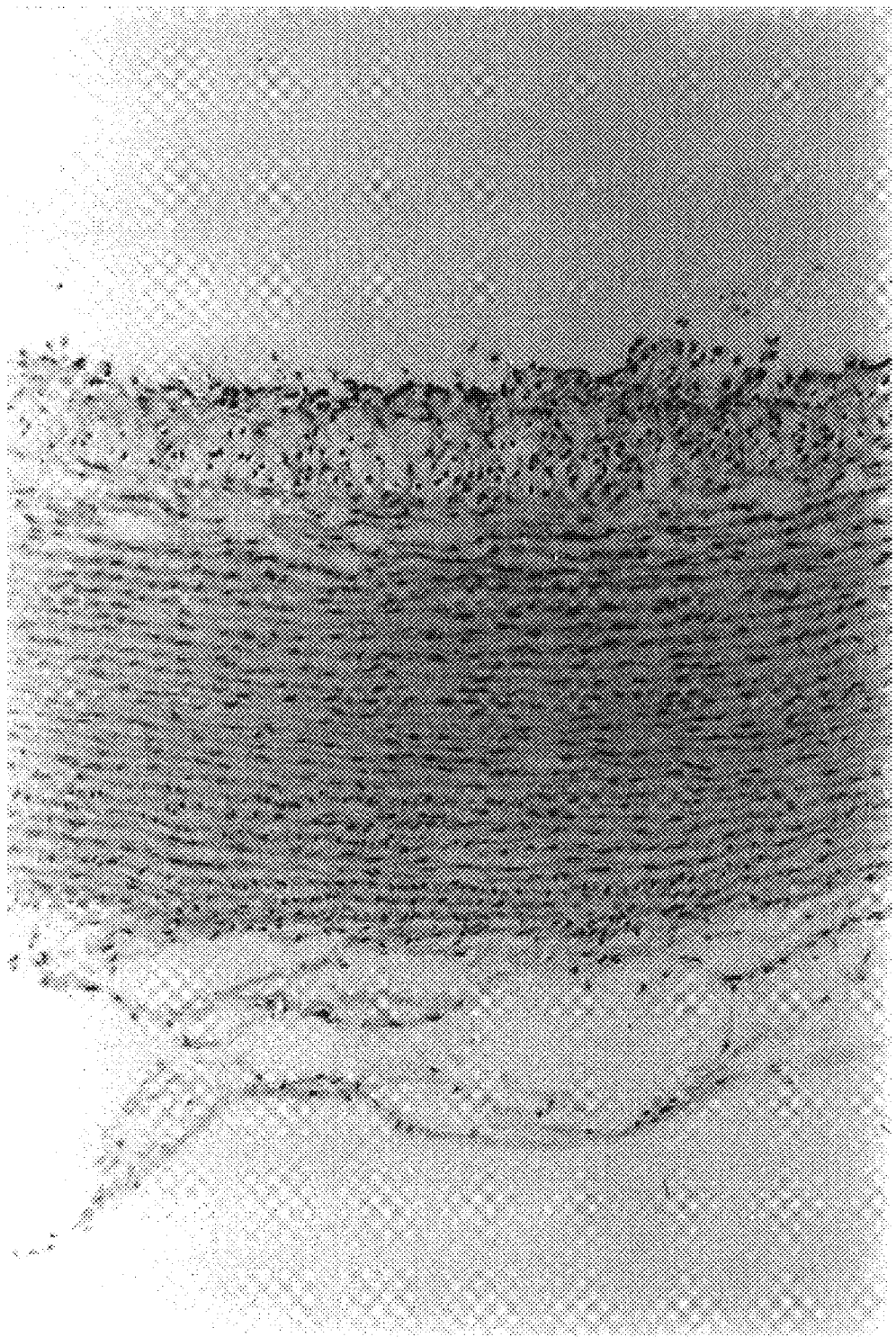
Figure 1D:
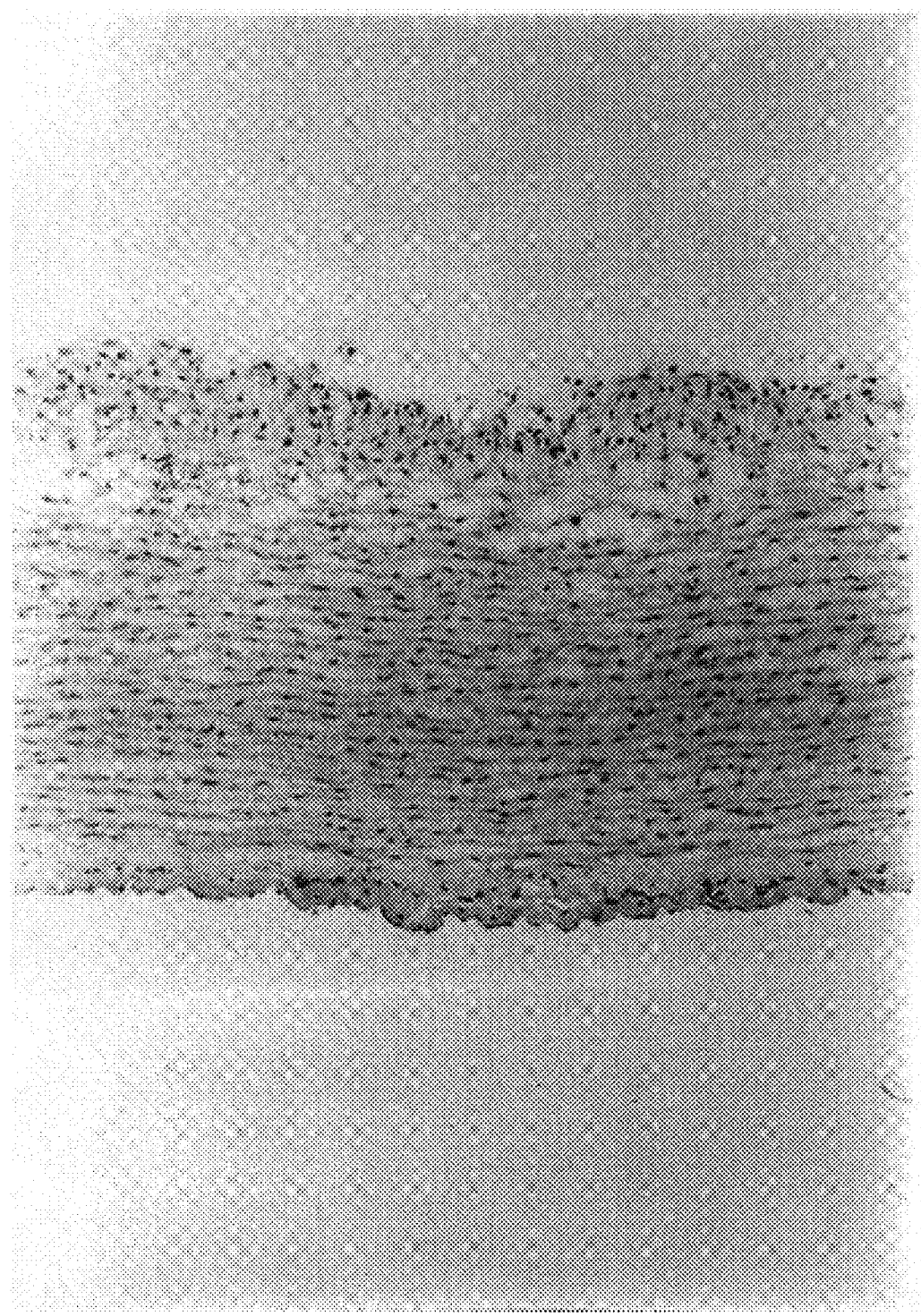
Figure 1E:
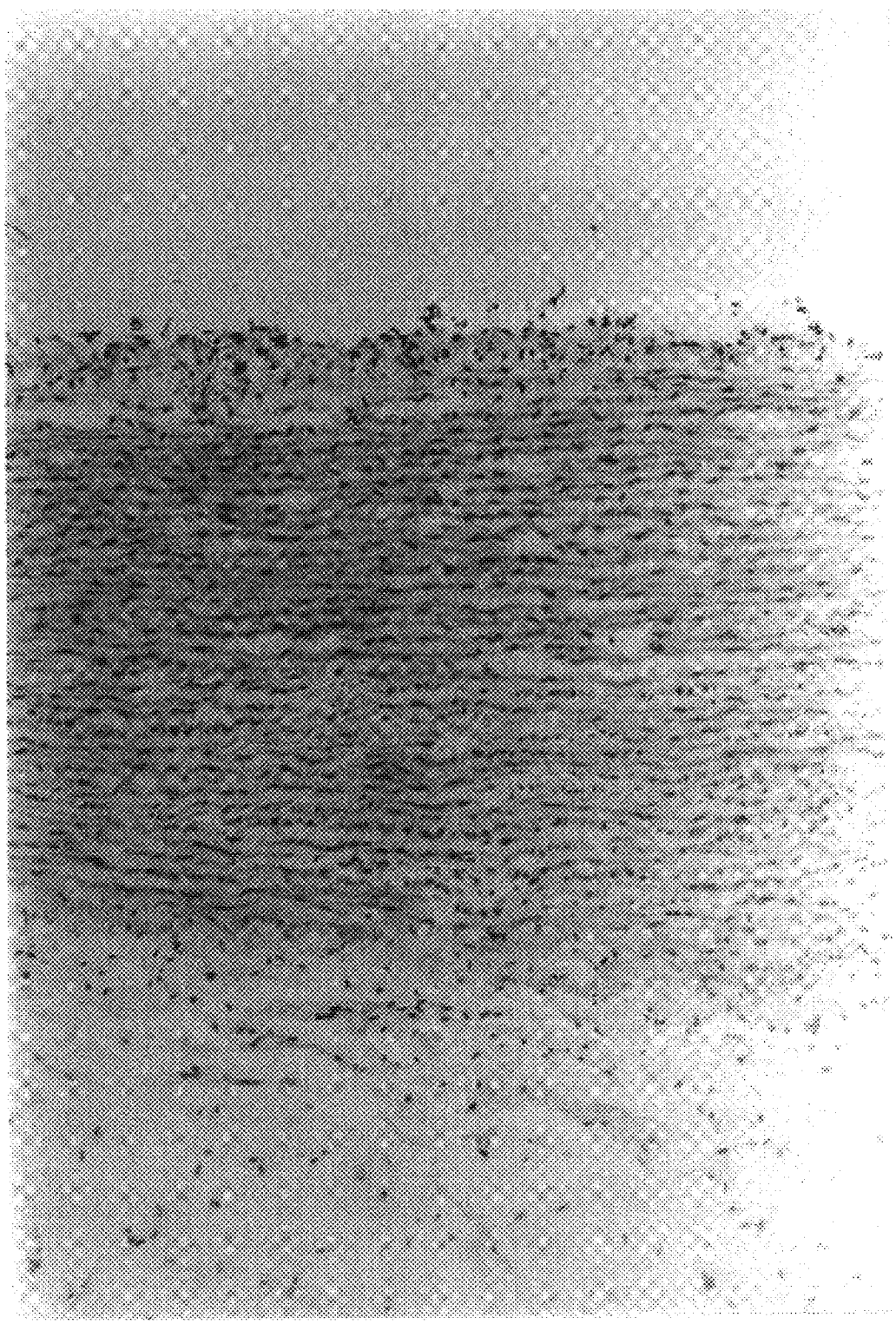

Throughout the specification, the term "blood lipid" designates a lipid present in the blood. The blood lipid is represented by cholesterol and triglycerides carried in the blood.

The term "high or elevated level" of a blood lipid means higher than normal level, the normal level varying with specific conditions of a patient, such as age, gender and body weight. A high level of blood lipid is ordinarily considered to be harmful to health.

The term "elevated blood lipid level-related disease" means a disease which is caused by a high or elevated level of blood lipid, and/or a disease whose symptoms include a high or elevated level of blood lipid. Examples of such a disease include hyperlipidemia, arteriosclerosis, angina pectoris, stroke, hepatic disease such as fatty liver and the like.

Preferable cinnamic acid derivatives of the present invention include the compounds of formula Ia or Ib wherein R$^1$, R$^2$, R$^3$ and R$^5$ are independently H or OH; R$^4$ is H, OH or OCH$_3$; and R$^6$ is H or a cycloalkyl substituted by one or more hydroxy groups and a carboxy group.

Representative but not limiting examples of the cinnamic acid derivatives of formula Ia or Ib include compounds of the following structures:

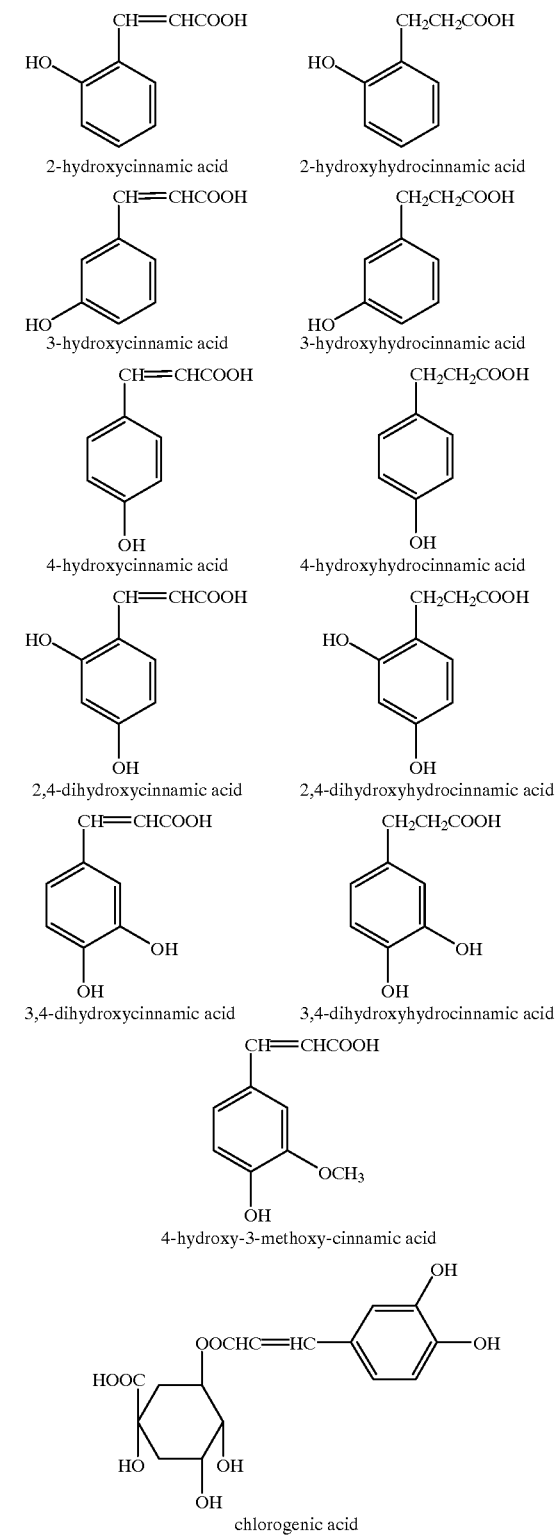

The cinnamic acid derivatives can be easily extracted from plants, e.g., apple, tea, potato, coffee, grape, nuts, strawberry, plum, cherry and blueberry, or synthesized in accordance with a conventional process.

Cinnamic acid derivatives exert inhibitory as well as therapeutic effects on elevated blood lipid level-related diseases, e.g., hyperlipidemia, arteriosclerosis, angina pectoris, stroke and hepatic disease. Further, in spite of their potent efficacies, cinnamic acid derivatives exhibit no toxicity when they are orally administered to a mouse at a dose of 1,000 mg/kg. Moreover, they do not adversely affect on the liver function.

The present invention provides a pharmaceutical composition for treating or preventing elevated blood lipid level-related diseases which comprises a cinnamic acid derivative in an effective amount together with a pharmaceutically acceptable excipients, carriers or diluents.

A pharmaceutical formulation may be prepared in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

Further, the pharmaceutical composition of the present invention can be administered via various routes including oral, transdermal, subcutaneous, intravenous and intramuscular introduction. In case of human, a typical daily dose of cinnamic acid derivatives may range from about 0.1 to 500 mg/kg body weight, preferably 1 to 100 mg/kg body weight, and can be administered in a single dose or in divided doses.

However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, cinnamic acid derivatives can be advantageously incorporated in foods or beverages for the purpose of treating or preventing elevated blood lipid level-related diseases. The foods or beverages may include meats; juices such as a vegetable juice (e.g., carrot juice and tomato juice) and a fruit juice (e.g., orange juice, grape juice, pineapple juice, apple juice and banana juice); chocolates; snacks; confectionery; pizza; food products made from cereal flour such as breads, cakes, crackers, cookies, biscuits, noodles and the likes; gums; dairy products such as milk, cheese, yogurt and ice creams; soups; broths; pastes, ketchups and sauces; teas; alcoholic beverages; carbonated beverages; vitamin complexes; and various health foods.

The content of the cinnamic acid derivatives in a food or beverage may range from 0.01 to 20 wt %, preferably, from 0.1 to 5 wt %.

As described above, cinnamic acid derivatives can be used as an effective, non-toxic pharmaceutical agent for treating or preventing elevated blood lipid level-related diseases, e.g., hyperlipidemia, arteriosclerosis and hepatic diseases.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Toxicity of Orally Administered 4-Hydroxycinnamic Acid 12 seven-week-old, specific pathogen-free ICR female mice, six female mice each weighing about 25 to 29 g and six male mice each weighing about 34 to 38 g, were kept under an environment of 22±1° C., 55±5% relative humidity and 12L/12D photoperiod. Fodder (Cheiljedang Co., mouse and rat fodder) and water were sterilized and fed to the mice.

4-hydroxycinnamic acid purchased from Aldrich-Sigma Chemical Co. (St. Louis, Mo., U.S.A) was dissolved in 0.5% Tween 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter, the weight changes of the mice were recorded to examine the effect of 4-hydroxycinnamic acid. Further, on the 10th day, the mice were sacrificed and the internal organs were visually examined.

All the mice were alive at day 10 and 4-hydroxycinnamic acid showed no toxicity at a dose of 1,000 mg/kg. The autopsy revealed that the mice had not developed any pathological abnormality, and no weight loss was observed during the 10 day test period. Accordingly, it was concluded that 4-hydroxycinnamic acid is not toxic when orally administered to an animal.

EXAMPLE 2

Effect of Cinnamic Acid Derivatives on Plasma Cholesterol, HDL-Cholesterol and Neutral Lipid Levels (Step 1) Administration of Cinnamic Acid Derivatives to Rats 40 three-week-old white Sprague-Dawley rats (Taihan laboratory animal center, Korea), each weighing about 90 to 110 g, were evenly divided into four dietary groups by a randomized block design. The rats of the four groups were fed with four different high-cholesterol diets, i.e., AIN-76 laboratory animal diet (ICN Biochemicals, Cleveland, Ohio, U.S.A.) containing 1% cholesterol (Control group); 1% cholesterol plus 0.1% 4-hydroxycinnamic acid (4-hydroxycinnamic acid group); 1% cholesterol plus 0.1% 3,4-dihydroxycinnamic acid (3,4-dihydroxycinnamic acid group); and 1% cholesterol plus 0.1% 3,4-dihydroxyhydrocinnamic acid (3,4-dihydroxyhydrocinnamic acid group), respectively. The compositions of the diets fed to the four groups are shown in Table I.

TABLE I

| Components | Dietary group | | | |
|---|---|---|---|---|
| | Control (n = 10) | 4-hydroxy-cinnamic acid (n = 10) | 3,4-dihydroxy-cinnamic acid (n = 10) | 3,4-dihydroxy-hydrocinnamic acid (n = 10) |
| Casein | 20 | 20 | 20 | 20 |
| D,L-methionine | 0.3 | 0.3 | 0.3 | 0.3 |
| Corn starch | 15 | 15 | 15 | 15 |
| Sucrose | 49 | 48.9 | 48.9 | 48.9 |
| Cellulose powder*[1] | 5 | 5 | 5 | 5 |
| Mineral mixture*[1] | 3.5 | 3.5 | 3.5 | 3.5 |
| Vitamin mixture*[1] | 1 | 1 | 1 | 1 |
| Choline citrate | 0.2 | 0.2 | 0.2 | 0.2 |
| Corn oil | 5 | 5 | 5 | 5 |
| Cholesterol | 1 | 1 | 1 | 1 |
| 4-Hydroxycinnamic acid*[2] | — | 0.1 | — | — |
| 3,4-dihydroxy-cinnamic acid*[2] | — | — | 0.1 | — |
| 3,4-dihydroxyhydro-cinnamic acid*[2] | — | — | — | 0.1 |
| Total (%) | 100 | 100 | 100 | 100 |

*[1]Purchased from TEKLAD premier Co. (Madison, WI, U.S.A.)
*[2]Purchased from Sigma Chemical Co. (St. Louis, MO, U.S.A.)

The rats were allowed to feed freely on the specified diet together with water for six weeks, the ingestion amount was recorded daily and the rats were weighed every 7 days, and then the record was analyzed. All rats showed a normal growth rate and there was observed no significant difference among the four groups in terms of the feed ingestion amount and the weight gain.

(Step 2) Determination of Total Cholesterol, HDL-cholesterol and Neutral Lipid Content in Blood The effects of administering cinnamic acid derivatives to rats on the plasma cholesterol and neutral lipid contents were determined as follows.

The rats of the four dietary groups obtained in Step 1 were sacrificed and blood samples were taken therefrom. The blood was allowed to stand for 2 hours and centrifuged at 3,000 rpm for 15 minutes and the supernatant was separated and stored in a deep freezer before use. The chemical analysis of blood was carried out by employing a blood chemical analyzer (CIBA Corning 550 Express, USA) to determine the changes in total cholesterol and HDL-cholesterol levels. The result is shown in Table II.

TABLE II

| Lipid Conc. | Group | | | |
|---|---|---|---|---|
| | Control | 4-Hydroxy-cinnamic acid | 3,4-dihydroxy cinnamic acid | 3,4-dihydroxy-hydro cinnamic acid |
| TC (mg/dl) | 135 ± 6 | 102 ± 6 | 118 ± 6 | 127 ± 4 |
| HDL-C (mg/dl) | 38 ± 2 | 57 ± 3 | 39 ± 3 | 45 ± 4 |
| $\frac{\text{HDL-C}}{\text{TC}}$ (%) | 28 | 56 | 33 | 35 |

*TC: Total cholesterol
*HDL-C: HDL-cholesterol

As can be seen from Table II, total plasma cholesterol level is reduced by 24%, 13% and 6% in the 4-hydroxycinnamic acid, 3,4-dihydroxycinnamic acid and 3,4-dihydroxyhydrocinnamic acid groups, respectively, as compared with that of the Control group. Further, the HDL-C/TC ratio is increased by 100%, 18% and 25% in the 4-hydroxycinnamic acid, 3,4-dihydroxycinnamic acid and 3,4-dihydroxyhydrocinnamic acid groups, respectively, as compared with that of the control group.

EXAMPLE 3

Activity of Cinnamic Acid Derivatives in ACAT Inhibition (Step 1) Preparation of Microsomes To determine the effect of feeding cinnamic acid derivatives to rats on the activity of ACAT, microsomes were separated from liver tissues to be used as an enzyme source.

1 g each of the livers taken from each group of rats of Example 2 was homogenized in 5 ml of homogenization medium (0.1 M $KH_2PO_4$, pH 7.4, 0.1 mM EDTA and 10 mM β-mercaptoethanol). The homogenate was centrifuged at 3,000×g for 15 min. at 4° C. and the supernatant thus obtained was centrifuged at 15,000×g for 15 min. at 4° C. to obtain a supernatant. The supernatant was put into an ultracentrifuge tube (Beckman) and centrifuged at 100,000×g for 1 hour at 4° C. to obtain microsomal pellets, which were then suspended in 3 ml of the homogenization medium and centrifuged at 100,000×g for 1 hour at 4° C. The pellets thus obtained were suspended in 1 ml of the homogenization medium. The protein concentration of the resulting suspension was determined by Lowry's method and then adjusted to 4 to 8 mg/ml. The resulting suspension was stored in a deep freezer (Biofreezer, Forma Scientific Inc.).

(Step 2) ACAT Assay 6.67 μl of 1 mg/ml cholesterol solution in acetone was mixed with 6 μl of 10% Triton WR-1339 (Sigma Co.) in acetone and, then, acetone was removed from the mixture by evaporation under a nitrogen flow. Distilled water was added to the resulting mixture to adjust the concentration of cholesterol to 30 mg/ml.

Added to 10 μl of the resulting aqueous cholesterol solution were 10 μl of 1 M $KH_2PO_4$(pH 7.4), 5 μl of 0.6 mM bovine serum albumin (BSA), 10 μl of microsome solution obtained in (Step 1) and 55 μl of distilled water (total 90 μl). The mixture was pre-incubated in a water bath at 37° C. for 30 min.

10 μl of (1-$^{14}$C) oleoyl-CoA solution (0.05 μCi, final concentration: 10 μM) was added to the pre-incubated mixture and the resulting mixture was incubated in a water bath at 37° C. for 30 min. Added to the mixture were 500 μl of isopropanol:heptane mixture (4:1 (v/v)), 300 μl of heptane and 200 μl of 0.1 M $KH_2PO_4$(pH 7.4), and the mixture was mixed vigorously using a vortex mixer and then allowed to stand at room temperature for 2 min.

200 μl of the resulting supernatant was put in a scintillation bottle and 4 ml of scintillation fluid (Lumac) was added thereto. The mixture was assayed for radioactivity with 1450 Microbeta liquid scintillation counter (Wallacoy, Finland). ACAT activity was calculated as picomoles of cholesteryl oleate synthesized per min. per mg protein (pmoles/min/mg protein). The result is shown in Table III.

TABLE III

| Group | Inhibition on ACAT activity (%) |
| --- | --- |
| Control | 0 |
| 4-Hydroxycinnamic acid | 17 |
| 3,4-Dihydroxycinnamic acid | 7 |
| 3,4-Dihydroxyhydrocinnamic acid | 20 |

As can be seen from Table III, ACAT activities observed in the 4-hydroxycinnamic acid, 3,4-dihydroxycinnamic acid and 3,4-dihydroxyhydrocinnamic acid groups are lower than that of the Control group by 7 to 20%.

EXAMPLE 4

Activity of Cinnamic Acid Derivatives in HMG-CoA Reductase Inhibition

In order to determine the activity of HMG-CoA reductase, Hulcher's method was employed after some modification (see *J. Lipid Res.*, 14, 625–641(1973)). In this method, the concentration of the coenzyme-A (CoA-SH), which is produced when HMG-CoA is reduced to a mevalonate salt by the action of HMG-CoA reductase, is determined by spectroscopy and the activity of HMG-CoA reductase is calculated therefrom.

(Step 1) Preparation of Microsomes 3 g of liver tissue taken from each group of rats of Example 2 was washed successively with 100 ml of a cold saline (0.15 M NaCl) and 100 ml of a cold buffer solution A (0.1 M triethanolamine, HCl/0.2 M EDTA/2 mM dithiothreitol (DTT)). The cold buffer solution A was added to the liver tissue in an amount of 2 ml per 1 g of the liver tissue and the mixture was homogenized with a homogenizer. The homogenate was centrifuged at 15,000×g for 15 minutes, and then, the supernatant was ultracentrifuged at 100,000×g for 60 minutes to obtain microsomal precipitates. The precipitates thus obtained was washed with a cold buffer solution A and kept in a 1.5 ml tube at −70° C.

(Step 2) HMG-CoA Reductase Activity Assay

The reaction substrates used in HMG-CoA reductase activity assay were as follows: i) buffer solution B: 0.1 M triethanolamine, HCl/0.02 M EDTA (pH 7.4), ii) HMG-CoA solution: 150 μmoles/culture medium, and iii) NADPH solution: 2 μmoles/culture medium.

The suspension (microsome) was mixed with the reaction substrate and the mixture was placed in a centrifugation tube and reacted at 37° C. for 30 minutes. The reaction mixture was treated with 20 μl of 0.01 M sodium arsenous and allowed to stand for 1 minute, and then it was reacted with 100 μl of citrate buffer solution (2 M citrate/3% sodium tungstate, pH 3.5) at 37°C. for 10 minutes followed by centrifugation at 25,000×g for 15 minutes to remove protein. 1 ml of the supernatant thus obtained was transferred into a tube with a cap and added thereto were 0.1 ml of 2 M tris-HCl solution (pH 10.6) and 0.1 ml of 2 M tris-HCl solution (pH 8.0) to adjust the pH of the reactant to 8.0.

Then, the reactant was mixed with 20 μl of DTNB buffer solution (3 mM DTNB/0.1 M triethanolamine/0.2 M EDTA, pH 7.4) and the absorbance of the mixture was determined at 412 nm to calculate the amount of CoA-SH (activity of HMG-CoA reductase).

The extent of inhibition of HMG-CoA reductase activity by cinnamic acid derivatives was calculated based on the above result. The result is shown in Table IV.

TABLE IV

| Group | Inhibition of HMG-CoA reductase activity (%) |
| --- | --- |
| Control | 0 |
| 4-Hydroxycinnamic acid | 31 |
| 3,4-dihydroxycinnamic acid | 44 |
| 3,4-dihydroxyhydrocinnamic acid | 70 |

As can be seen in Table IV, the HMG-CoA reductase activities observed with the 4-hydroxycinnamic acid, 3,4-dihydroxycinnamic acid and 3,4-dihydroxyhydrocinnamic acid groups are lower than that of the Control group by 31 to 70%.

EXAMPLE 5

Effect of Cinnamic Acid Derivatives in Rabbits

Step 1) Administration of Cinnamic Acid Derivatives to Rabbits 30 three-month-old male New Zealand White rabbits (Yeonam Horticulture and Animal Husbandry College, Korea), each weighing about 2.5 to 2.6 kg, were raised under condition of temperature 20±2° C., relative humidity 55±5%, and photoperiod 12L/12D. The rabbits were divided into 5 groups and 5 groups of rabbits were fed with 5 different diets, i.e., RC4 diet (Oriental Yeast Co., Japan) containing 1% cholesterol (Control group); 1% cholesterol plus 1 mg/kg Lovastatin® (Merck, U.S.A.) (Lovastatin group); 1% cholesterol plus 0.1% 4-hydroxycinnamic acid (4-hydroxycinnamic acid group); 1% cholesterol plus 0.1% 3,4-dihydroxycinnamic acid (3,4-dihydroxycinnamic acid group); and 1% cholesterol plus 0.1% 3,4-dihydroxyhydrocinnamic acid (3,4-dihydroxyhydrocinnamic acid group), respectively. RC4 diet comprises 7.6% moisture, 22.8% crude protein, 2.8% crude fat, 8.8% crude ash, 14.4% crude cellulose and 43.6% soluble nitrogen-free substances. Cinnamic acid derivatives were purchased from Sigma Chemical Co. (St. Louis, Mo.).

The rabbits were fed for 8 weeks while being allowed free access to the diets and water.

(Step 2) Chemical Analysis of Blood

After eight weeks, the rabbits were anesthetized with an intramuscular injection of ketamine (50 mg/kg) in the femoral region and sacrificed. A blood sample was taken from the heart of each rabbit, allowed to stand for 2 hours and centrifuged at 3,000 rpm for 15 minutes and the supernatant serum was separated and stored in a freezer before use.

The chemical analysis of blood was carried out by employing a blood chemical analyzer (CIBA Corning 550 Express, USA) to determine the changes in GOT, GPT, total cholesterol, HDL-cholesterol and triglyceride levels. The result is shown in Table V.

(Step 3) Analysis for Fatty Streak in the Main Artery

The chest of each of the rabbits sacrificed in Step 2 was incised. The downward portion of the main artery from the site 1 cm above the aortic valve was cut out in a length of about 5 cm and the fat surrounding the main artery was removed. The main artery was incised in the middle along the longitudinal axis and pinned to a dish. The moist artery was photographed and, then, the staining of fatty streaks was carried out in accordance with the method of Esper, E., et al. (*J. Lab. Clin. Med.*, 121, 103–110(1993)) as follows.

A part of the incised main artery was washed three times with anhydrous propylene glycol for 2 min. and stained for 30 min. with a saturated solution of Oil Red O (ORO, Sigma Co.) dissolved in propylene glycol. Thereafter, the artery was washed twice with 85% propylene glycol for 3 min. to remove remaining staining solution and, then washed with physiological saline. The artery was photographed and the photograph was traced. The area of stained region (fatty streak region) was determined with an image analyzer (LEICA, Q-600, Germany) and its proportion (%) to the total arterial area was calculated. The result is shown in Table V.

FIGS. 1A, 1B, 1C, 1D and 1E show the arteries of the rabbits of the Control, Lovastatin, 4-hydroxycinnamic acid, 3,4-dihydroxycinnamic acid, and 3,4-dihydroxyhydrocinnamic acid groups, respectively. As shown in FIGS. 1A, 1B, 1C, 1D and 1E, a thick layer of macrophage-lipid complex was observed on the arterial endothelium of the rabbit of the control group, while no or very thin layers of macrophage-lipid complex were observed on the arterial endothelia of the rabbits of the Lovastatin, 4-hydroxycinnamic acid, 3,4-dihydroxycinnamic acid and 3,4-dihydroxyhydrocinnamic acid groups.

Accordingly, it is concluded that the cinnamic acid derivatives strongly inhibits the deposition of macrophages on the arterial endothelium even when the blood cholesterol level is high.

(Step 4) Histologic Observation of the Organs

Portions of the main artery, heart, lung, liver, kidney and muscle were taken from each of the rabbits sacrificed in step 2 and visually examined to confirm that no pathogenic abnormality was found. One half of each portion of the organs was deep freezed and the other half was fixed in 10% neutral buffered formalin for more than 24 hours. The fixed organ piece was washed sufficiently with tap water, dehydrated stepwise with 70%, 80%, 90% and 100% ethanol and, then, embedded in a paraffin by employing SHANDON®, Histocentre 2, USA. The embedded organ piece was sectioned in 4 μm thickness with a microtome (LSICA, RM2045, Germany) and stained with hematoxylin and eosin. The stained organ specimen was made transparent with xylene, mounted with permount, and then observed under a microscope to look for the presence of lesions. No lesion was observed in any of the organ specimen.

(Step 5) Prevention of Hepatic Diseases

In order to evaluate the effects of feeding a high cholesterol diet with cinnamic acid derivatives on liver tissues, the liver specimens taken from the sacrificed rabbit in Step 2 were treated in accordance with the procedure disclosed in Fogt F. and Nanji A., Toxicology and Applied Pharmacology, 136, 87–93, 1996; and Keegan A., et al., Journal of Hepatology 23: 591–600, 1995, and observed under a microscope to be classified into four grades, i.e., 1+(0–25%), 2+(26–50%), 3+(51–75), 4+(76–100%) based on the roportion of abnormal fat-containing cells around the central vein in the liver acinus. The result is shown in Table V.

Figure 2A:
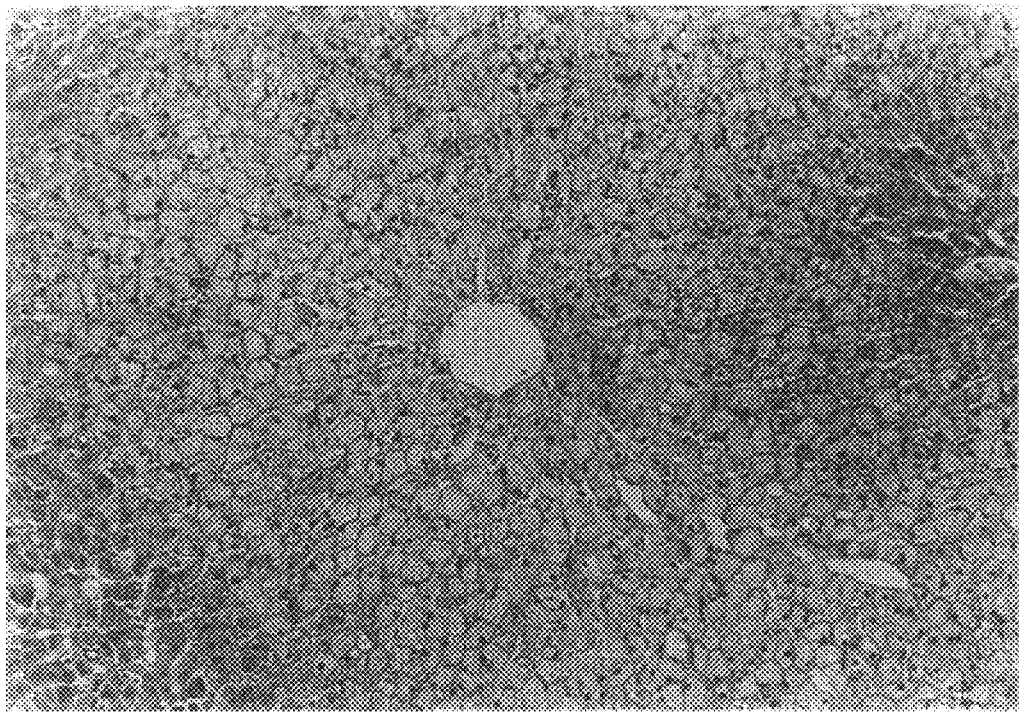
FIGS. 2A, 2B, 2C, 2D and 2E present the microscopic features of the livers of the rabbits administered with 1% cholesterol; 1% cholesterol plus 1 mg/kg Lovastatin®; 1% cholesterol plus 0.1% 4-hydroxycinnamic acid; 1% cholesterol plus 0.1% 3,4-dihydroxycinnamic acid; and 1% cholesterol plus 0.1% 3,4-dihydroxyhydrocinnamic acid, respectively.
Figure 2B:
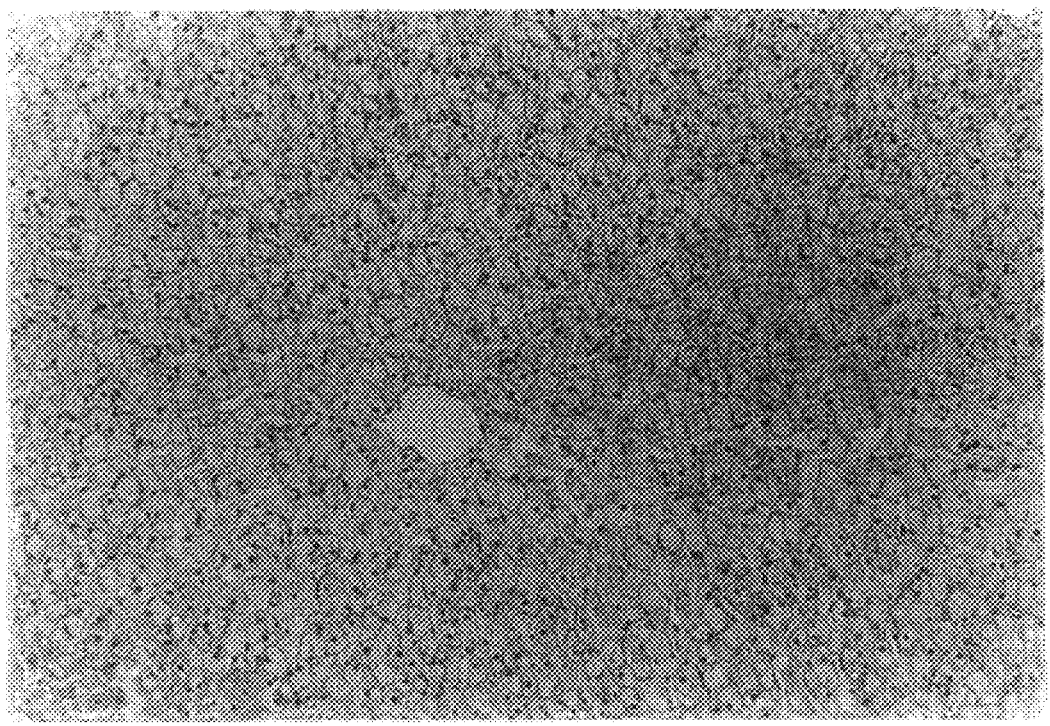
Figure 2C:
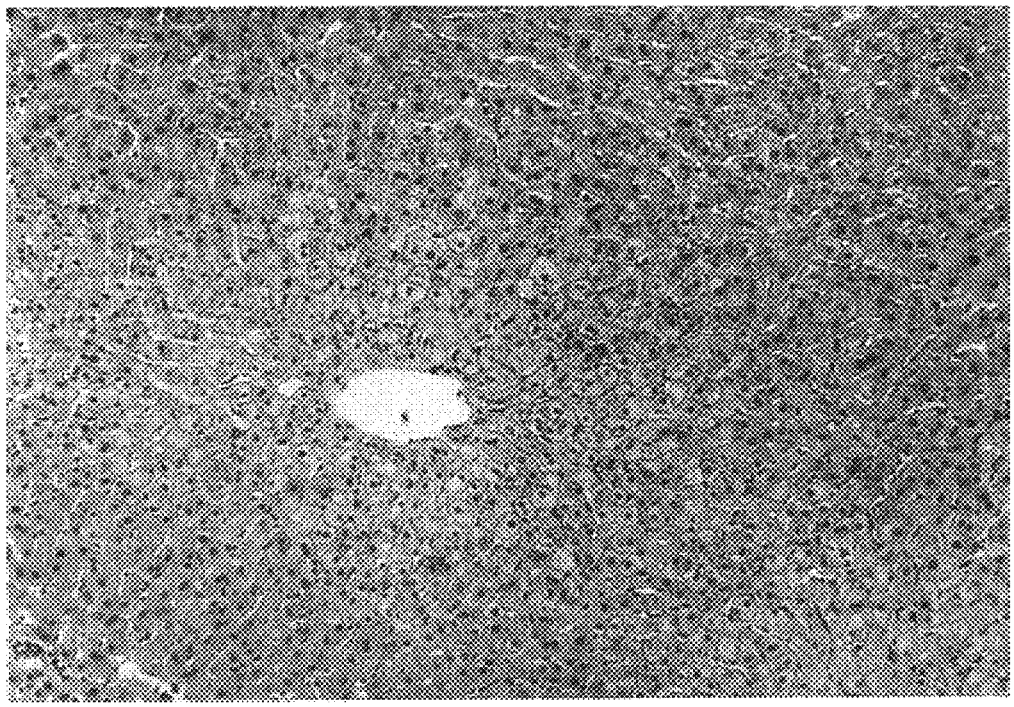
Figure 2D:
Figure 2E:

FIGS. 2A, 2B, 2C, 2D and 2E present the microscopic features of the livers of the rabbits of the control, Lovastatin, 4-hydroxycinnamic acid, 3,4-dihydroxycinnamic acid and 3,4-dihydroxyhydrocinnamic acid groups. In FIGS. 2A and 2B, many cells containing excessive fat were observed around the central vein. In contrast, almost all liver cells are of a normal shape in FIGS. 2C, 2D and 2E, which suggested that cinnamic acid derivatives can significantly inhibit the formation of fatty liver.

As can be seen from the above, the administration of cinnamic acid derivatives can improve lipid metabolism in rabbit and liver function and inhibit the plaque formation in the endothelium of the main artery and formation of fatty liver as shown in Table V. The results were tested by student t-test by using Microsoft excel (version 7.0) program.

TABLE V

| Group | TC (mg/dl) | TG (mg/dl) | HDL-C (mg/dl) | HDL/TC (%) | GOT (IU/l) | GPT (IU/l) | Fatty streak (%) | A |
|---|---|---|---|---|---|---|---|---|
| Control | 1995 ± 472 | 170 ± 30 | 50 ± 11 | 2.5 ± 0.4 | 161 ± 71 | 96 ± 46 | 80 ± 8 | 3.2 ± 0.3 |
| Lovastatin | 1446 ± 263 | 153 ± 95 | 58 ± 23 | 4.9 ± 2.6 | 43 ± 12 | 81 ± 44 | 15 ± 3 | 3.4 ± 0.5 |
| 4-Hydroxycinnamic acid | 1517 ± 417 | 167 ± 43 | 57 ± 28 | 3.7 ± 1.3 | 59 ± 45 | 74 ± 49 | 24 ± 11 | 2.7 ± 0.3 |
| 3,4-dihydroxycinnamic acid | 1559 ± 347 | 139 ± 46 | 53 ± 13 | 3.4 ± 0.4 | 99 ± 49 | 40 ± 27 | 13 ± 5 | 2.6 ± 0.3 |
| 3,4-dihydroxyhydro-cinnamic acid | 1256 ± 150 | 108 ± 22 | 80 ± 23 | 6.3 ± 1.6 | 55 ± 20 | 90 ± 83 | 16 ± 1 | 2.6 ± 0.3 |

*TC: Total cholesterol
*TG: Triglyceride
*HDL-C: High density lipoprotein-cholesterol
A: Proportion of abnormal fat-containing liver cells As can be seen from Table V, administration of 4-ydroxycinnamic acid, 3,4-dihydroxycinnamic acid and 3,4-dihydroxyhydrocinnamic acid lowers serum triglyceride level by 22 to 37%, as compared to the Control group. Further, administration of the cinnamic acid derivatives lowers serum GOT and GPT levels by 10 to 36% and 6 to 58%, respectively, as compared to the Control group. Moreover, administration of the cinnamic acid derivatives significantly inhibits the formation of fatty liver as compared to the Control group and the Lovastatin group.

Accordingly, cinnamic acid derivatives can be used as an effective, non-toxic pharmaceutical agent for treating or preventing elevated blood lipid level-related diseases, e.g., hyperlipidemia, arteriosclerosis and hepatic diseases.

EXAMPLE 6

Activity of Cinnamic Acid Derivatives in ACAT Inhibition in Rabbits

The activity of cinnamic acid derivatives in ACAT Inhibition was examined in Rabbits prepared in Step 1 of Example 5 in accordance with the method of Example 3. The result is shown in Table VI.

TABLE VI

| Group | Inhibition on ACAT activity (%) |
| --- | --- |
| Control | 0 |
| 4-Hydroxycinnamic acid | 9 |
| 3,4-Dihydroxycinnamic acid | 33 |
| 3,4-Dihydroxyhydrocinnamic acid | 37 |

As can be seen from Table VI, the ACAT activities observed in the 4-hydroxycinnamic acid, 3,4-dihydroxycinnamic acid and 3,4-dihydroxyhydrocinnamic acid groups are lower than that of the control group by 9 to 37%.

EXAMPLE 7

Effect of Administration of 4-Hydroxycinnamic Acid to a Human on Plasma Lipid Metabolism Two men in their mid-fifties, suffered by hyperlipidemia with blood cholesterol level ranging from 230 to 270 mg/dl and blood triglyceride level ranging from 200 to 220 mg/dl, were administered with a daily oral dose of 10 mg/kg of 4-hydroxycinnamic acid in the form of a capsule for 60 days. The plasma cholesterol and triglyceride contents were determined before and after the administration.

The plasma cholesterol and triglyceride contents were reduced by the 4-hydroxycinnamic acid administration by 25% and 20%, respectively.

FORMULATION 1

Preparation of Pharmaceutical Formulation

Hard gelatin capsules were prepared using the following ingredients:

|  | Quantity (mg/capsule) |
| --- | --- |
| Active ingredient (4-hydroxycinnamic acid) | 200 |
| Vitamin C | 50 |
| Lactose (carrier) | 150 |
| Total | 400 |

The above ingredients were mixed thoroughly and filled in a hard gelatin capsule.

FORMULATION 2

Foods Containing Cinnamic Acid Derivatives

Foods containing cinnamic acid derivatives were prepared as follows.

(1) Preparation of Tomato Ketchup and Sauce

4-Hydroxycinnamic acid, 3,4-dihydroxycinnamic acid or 3,4-dihydroxyhydrocinnamic acid was added to a tomato ketchup or sauce in a sufficient amount to obtain a health-improving tomato ketchup or sauce containing 0.1 to 5 wt % of 4-Hydroxycinnamic acid, 3,4-dihydroxycinnamic acid or 3,4-dihydroxyhydrocinnamic acid.

(2) Preparation of Foods Containing Wheat Flour

4-Hydroxycinnamic acid, 3,4-dihydroxycinnamic acid or 3,4-dihydroxyhydrocinnamic acid was added to wheat flour in a sufficient amount to obtain a wheat flour mixture containing 0.1 to 5 wt % of 4-Hydroxycinnamic acid, 3,4-dihydroxycinnamic acid or 3,4-dihydroxyhydrocinnamic acid, and breads, cakes, cookies, crackers and noodles were prepared by using the mixture to obtain health-improving foods.

(3) Preparation of Soups and Gravies

4-Hydroxycinnamic acid, 3,4-dihydroxycinnamic acid or 3,4-dihydroxyhydrocinnamic acid was added to soups and gravies in a sufficient amount to obtain health-improving soups and gravies containing 0.1 to 5 wt % of 4-Hydroxycinnamic acid, 3,4-dihydroxycinnamic acid or 3,4-dihydroxyhydrocinnamic acid.

(4) Preparation of Ground Beef

4-Hydroxycinnamic acid, 3,4-dihydroxycinnamic acid or 3,4-dihydroxyhydrocinnamic acid was added to ground beef in a sufficient amount to obtain health-improving ground beef containing 0.1 to 5 wt % of 4-Hydroxycinnamic acid, 3,4-dihydroxycinnamic acid or 3,4-dihydroxyhydrocinnamic acid.

(5) Preparation of Dairy Products

4-Hydroxycinnamic acid, 3,4-dihydroxycinnamic acid or 3,4-dihydroxyhydrocinnamic acid was added to milk in a sufficient amount to obtain milk containing 0.1 to 5 wt % of 4-Hydroxycinnamic acid, 3,4-dihydroxycinnamic acid or 3,4-dihydroxyhydrocinnamic acid, and various dairy products such as butter and ice cream were prepared therefrom.

In case of a cheese preparation, 4-Hydroxycinnamic acid, 3,4-dihydroxycinnamic acid or 3,4-dihydroxyhydrocinnamic acid was added to coagulated milk protein; and, in case of a yogurt preparation, the cinnamic acid derivative was added to coagulated milk protein obtained after the fermentation.

(6) Hamburger Sauce Containing Cinnamic Acid Derivatives

A hamburger sauce was prepared by employing the following materials in accordance with a conventional method: 20% tomato, 20% onion, 7% garlic, 10% jujube, 10% raisin powder, 20% oatmeal powder, 10% potato powder and 3% 4-hydroxycinnamic acid, 3,4-dihydroxycinnamic acid or 3,4-dihydroxyhydrocinnamic acid.

10 g of the hamburger sauce thus obtained was applied on a hamburger.

FORMULATION 3

Beverages Containing Cinnamic Acid Derivatives

4-Hydroxycinnamic acid, 3,4-dihydroxycinnamic acid or 3,4-dihydroxyhydrocinnamic acid was added to source materials for the preparation of a vegetable or fruit juice to obtain a health-improving juice containing 0.01 to 20 wt % of 4-Hydroxycinnamic acid, 3,4-dihydroxycinnamic acid or 3,4-dihydroxyhydrocinnamic acid.

While the invention has been described with respect to the above specific embodiments, it should be recognized that various modifications and changes may be made to the invention by those skilled in the art which also fall within the scope of the invention as defined by the appended claims.

What is claimed is:

1. A method for treating or preventing an elevated blood lipid level-related disease in a mammal in need thereof, which comprises administering thereto an effective amount of a hydroxycinnamic acid derivative of formula Ia or Ib, or a pharmaceutically acceptable salt thereof:

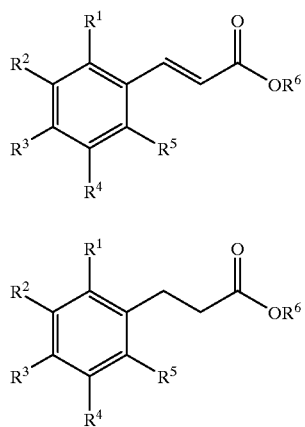

wherein,
$R^1$, $R^2$, $R^4$ and $R^5$ are independently H, OH or $C_{1-4}$ alkoxy;
$R^3$ is H or OH; and
$R^6$ is H, $C_{1-4}$ alkyl group, or $C_{5-7}$ cycloalkyl group having one or more substituents selected from the group consisting of OH, alkoxy and carboxy groups,
with the proviso that not all of $R^1$, $R^2$, $R^3$, $R^4$ and $R^5$ are simultaneously H.

2. The method of claim 1, wherein the disease is hyperlipidemia, arteriosclerosis, angina pectoris, stroke or fatty liver.

3. The method of claim 1, wherein the mammal is human.

4. The method of claim 1, wherein the hydroxycinnamic acid derivative is one of those wherein $R^1$, $R^2$, $R^3$ and $R^5$ are independently H or OH; $R^4$ is H, OH or $OCH_3$; and $R^6$ is H or a cycloalkyl group substituted by one or more hydroxy groups and a carboxy group.

5. The method of claim 1, wherein the hydroxycinnamic acid derivative is 4-hydroxycinnamic acid, 3,4-dihydroxycinnamic acid, or 3,4-dihydroxyhydrocinnamic acid.

6. The method of claim 1, wherein the hydroxycinnamic acid derivative is administered in the form of a pharmaceutical composition containing an effective amount of hydroxycinnamic acid derivative and pharmaceutically acceptable excipients, carriers or diluents.

7. The method of claim 6, wherein the effective amount of the hydroxycinnamic acid derivative ranges from 0.1 to 500 mg/kg of body weight/day.

8. The method of claim 1, wherein the hydroxycinnamic acid derivative is administered in the form of a health-improving food composition containing the hydroxycinnamic acid derivative in an amount ranging from 0.01 to 20 wt %.

9. The method of claim 8, wherein the food is meat, chocolate, snack, confectionery, pizza, a health food product or a food product made from cereal flour, gums, dairy products, soups, broths, pastes, ketchups, sauces or vitamin complexes.

10. The method of claim 9, wherein the food product made from cereal flour is bread, cake, cracker, cookie, biscuit or noodle.

11. The method of claim 9, wherein the dairy product is milk, ice cream, cheese or yogurt.

12. The method of claim 1, wherein the hydroxycinnamic acid derivative is administered in the form of a health-improving beverage composition containing the hydroxycinnamic acid derivative in an amount ranging from 0.01 to 20 wt %.

13. The method of claim 12, wherein the beverage is a vegetable juice, fruit juice, tea, alcoholic beverage or carbonated beverage.

* * * * *

UNITED STATES PATENT AND TRADEMARK OFFICE
CERTIFICATE OF CORRECTION

PATENT NO.   : 6,313,171 B1
DATED        : November 6, 2001
INVENTOR(S)  : Song-Hae Bok et al.

It is certified that error appears in the above-identified patent and that said Letters Patent is hereby corrected as shown below:

<u>Title page,</u>
Item [75], please add inventor: -- Sang-Ku Lee, of Daejon --

Signed and Sealed this

Third Day of December, 2002

JAMES E. ROGAN
*Director of the United States Patent and Trademark Office*